United States Patent
Köck et al.

(10) Patent No.: US 10,226,445 B2
(45) Date of Patent: *Mar. 12, 2019

(54) PHARMACEUTICAL PREPARATIONS

(71) Applicant: Symrise AG, Holzminden (DE)

(72) Inventors: Elke Köck, Neumarkt (AT); Jakob Ley, Holzminden (DE); Veronika Somoza, Weidling (AT); Kathrin Liszt, Rechnitz (AT); Sabine Widder, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/761,474

(22) PCT Filed: Jan. 15, 2014

(86) PCT No.: PCT/EP2014/050742
§ 371 (c)(1),
(2) Date: Nov. 4, 2015

(87) PCT Pub. No.: WO2014/111436
PCT Pub. Date: Jul. 24, 2014

(65) Prior Publication Data
US 2016/0081977 A1 Mar. 24, 2016

(30) Foreign Application Priority Data
Jan. 17, 2013 (EP) .................... 13151578

(51) Int. Cl.
| | | |
|---|---|---|
| *A61K 31/365* | (2006.01) | |
| *A23L 33/10* | (2016.01) | |
| *A23F 3/40* | (2006.01) | |
| *A23F 5/46* | (2006.01) | |
| *G01N 33/50* | (2006.01) | |
| *A23L 2/52* | (2006.01) | |
| *A61K 47/22* | (2006.01) | |
| *A61K 31/341* | (2006.01) | |
| *A61K 31/353* | (2006.01) | |
| *A23L 27/00* | (2016.01) | |
| *A61K 9/00* | (2006.01) | |
| *A61K 9/68* | (2006.01) | |
| *A61K 9/19* | (2006.01) | |
| *A61K 9/48* | (2006.01) | |

(52) U.S. Cl.
CPC .......... *A61K 31/365* (2013.01); *A23F 3/405* (2013.01); *A23F 5/465* (2013.01); *A23L 2/52* (2013.01); *A23L 27/86* (2016.08); *A23L 33/10* (2016.08); *A61K 31/341* (2013.01); *A61K 31/353* (2013.01); *A61K 47/22* (2013.01); *G01N 33/5044* (2013.01); *A23V 2002/00* (2013.01); *A61K 9/0056* (2013.01); *A61K 9/0058* (2013.01); *A61K 9/0095* (2013.01); *A61K 9/19* (2013.01); *A61K 9/4875* (2013.01)

(58) Field of Classification Search
CPC ........ A61K 31/365; A23L 33/10; A23L 27/86
See application file for complete search history.

(56) References Cited

U.S. PATENT DOCUMENTS

| | | | | |
|---|---|---|---|---|
| 8,685,436 | B2 * | 4/2014 | Ley | A23F 3/405 424/439 |
| 8,778,987 | B2 * | 7/2014 | Ley | C07C 49/83 426/3 |
| 8,992,892 | B2 * | 3/2015 | Backes | A23L 1/236 424/49 |
| 9,131,716 | B2 * | 9/2015 | Backes | A23L 1/22664 |
| 9,198,451 | B2 * | 12/2015 | Riess | A23L 1/2366 |
| 9,386,787 | B2 * | 7/2016 | Krammer | A23F 3/163 |
| 9,545,119 | B2 * | 1/2017 | Backes | A23L 27/84 |
| 2002/0106388 | A1 * | 8/2002 | Pugliese | A61K 8/44 424/401 |
| 2002/0188019 | A1 * | 12/2002 | Ley | A23F 3/405 514/456 |
| 2004/0156881 | A1 * | 8/2004 | Cassidy | A23L 33/11 424/439 |
| 2010/0151055 | A1 * | 6/2010 | Riess | A23L 1/2366 424/679 |
| 2010/0292175 | A1 * | 11/2010 | Wessjohann | C07D 311/60 514/23 |
| 2014/0050835 | A1 * | 2/2014 | Backes | A23L 1/22075 426/536 |

OTHER PUBLICATIONS

Ley et al. J. Agric. Food Chem., 2005, vol. 53, pp. 6061-6066.*
Caffeine Content of Popular Drinks (Accessed from https://web.archive.org/web/20130105041909/https://www.math.utah.edu/~yplee/fun/caffeine.html on Jun. 22, 2017) (originally available on Jan. 5, 2013).*
Ley et al. J. Agric. Food Chem., 2012, vol. 60, pp. 6303-6311 (Year: 2012).*
Liu et al. Journal of Chinese Pharmaceutical Sciences, 2013, vol. 22, No. 5, pp. 427-430 (Year: 2013).*
Monforte et al. "Protective Effect of Calamintha officinalis Moench Leaves against Alcohol-induced Gastric Mucosa Injury in Rats, Macroscopic, Histologic and Phytochemical Analysis," Phytother. Res. vol. 26, No. 6, Jun. 10, 2012, pp. 839-844.

* cited by examiner

*Primary Examiner* — James D. Anderson
(74) *Attorney, Agent, or Firm* — Dilworth & Barrese, LLP

(57) ABSTRACT

Pharmaceutical preparations are proposed, comprising bitter-masking acting substances for reducing and/or inhibiting gastric acid secretion induced by food constituents.

12 Claims, 2 Drawing Sheets

Proton secretion on exposure to caffeine or caffeine/enterolactone

Proton secretion on exposure to enterolactone

PHARMACEUTICAL PREPARATIONS

FIELD OF THE INVENTION

The invention is in the fields of pharmaceuticals and foodstuffs and relates to preparations comprising active ingredients against secretion of gastric acid induced by food constituents.

PRIOR ART

The stimulation of gastric acid secretion is an important mechanism to initiate the digestion of food, especially protein-rich food. It may be quite positive in terms of digestion to activate short-term moderate additional secretion. However, if gastric acid is excessively secreted due to external stimuli and the pH in the stomach is thus greatly reduced, this generally leads to acute discomfort or acid reflux. If this condition persists for a relatively long time or gastric acid secretion is chronically highly activated, inflammatory conditions of the gastric mucosa and the esophagus may be induced, which in turn, as a long-term consequence, trigger ulcers and, in the worst case, even malignant tissue alterations up to stomach cancer and esophageal cancer.

Gastric acid secretion is also induced, in addition to general stimuli such as food intake or hunger states etc, by diverse low molecular weight food constituents. For example, Liszt et al. in J. Agric Food Chem. 60, 7022-7030 (2012) describe that the fruit acids malic acid and succinic acid increasingly present in white wine make a substantial contribution to excess acid secretion which can however be mitigated again by alcohol in the case of tartaric acid. Hop constituents, e.g. via beer consumption, can also induce release of protons into the stomach contents (cf. Walker et al. in J. Agric Food Chem. 60, 1405-1412 (2012), in which a trend of the relative bitterness and the activity on proton secretion can be observed. Also coffee, and in particular the caffeine present therein, is able to significantly stimulate gastric acid secretion, as has been shown by Rubach et al., in Mol. Nutr. Food Res. 56, 325-335 (2012).

Classically, two major groups of active ingredients are used for reducing the gastric acid secretion described above: firstly, neutralization of the gastric acid to increase the pH with the aid of basic materials such as sodium hydrogen carbonate, calcium carbonate, basic aluminum hydroxide or magnesium hydroxide etc.; secondly, decreasing the gastric acid secretion by direct blocking of the acetyl choline receptors ($M_3$ type) to be found on the secretory cells (parietal cells) by active ingredients such as pirenzepin or, more frequently, histamine $H_2$-receptors, e.g. by active ingredients such as cimetidine, ranitidine or famotidine; as a third mode of action, the ATP-driven proton pump of the parietal cells is directly modulated (omeprazole).

The mechanism of the stimulatory activity of the aforementioned food constituents is generally unclear. It is therefore also not possible to predict which low molecular weight substances used for or in food (except basic substances due to their buffer effect) may even possibly reverse the effect and thus may reduce the excess secretion.

From the article of M. T. Montforte et al. entitled "Protective Effect of *Calamintha officinalis* (monk's leaves) against alcohol-induced gastric mucosa injury in rats", it is apparent that extracts of *Calamintha officinalis*, known in Italy as "culinary herb" under the name *Mentuccia*, have a gastroprotective effect in animal experiments. The extracts here comprise polyphenols, catechins, tannins and terpenes such as eriocitrin, eriodyctiol, benzoic acid, chlorogenic acid and others. The gastroprotective effect was confirmed in this case by the reduced formation of stomach tumors (cf. Phytother. Res. 26(6), pp. 839-844 (2012).

The publication of M. Trautmann et al. entitled "Aspirin-like drugs, ethanol-induced rat gastric injury and mucosal eicosanoid release" relates to the influence of aspirin and other active ingredients similar to salicylic acids on the release of leukotrienes and prostaglandins. In this case, salicylamide is known as one of the substances which inhibit the secretion of leukotrienes and thus has a gastroprotective effect (cf. Europ. J. Pharmacol. 201(1), pp. 53-58 (1991).

The article of R. Magous et al. entitled "Leukotrienes stimulate acid secretion from isolated gastric parietal cells" is concerned with leukotrienes, which stimulate a mild contraction of the muscles in the stomach region. It should be noted that specific leukotrienes stimulate acid secretion in isolated gastric cells from hares (cf. Biochem. Biophys. Res. Comm. 114(3), pp. 897-900 (1983).

The publication of M. B. Eswaran et al. entitled "Gastroprotective activity of *Cinnamonium tamala* leaves on experimental gastric ulcers in rats" relates to the gastroprotective properties of, for example, eugenol and other active ingredients from the leaves of *Cinnamomum tamala* (cf. J. Ethnopharm. 128(2), pp. 537-540 (2010).

The document of G. Kaithwas et al. entitled "Evaluation of antiulcer and antisecretory potential of *Linum usitatissimum* fixed oil." relates to the use of linseed oil for gastroprotective purposes (cf. Inflammopharm. 18(3), pp. 137-145 (2010).

This publication of I. Gurbuz et al. entitled "Anti-ulcerogenic lignans from *Taxus boccata*" concerns the use of lignans, specifically resinols from *Taxus* in cancer therapy (cf. Z. f. Naturforsch. 59c, pp. 233-236 (2004).

U.S. Pat. No. 4,865,847 (GOSSWEIN) relates to a method for preventing stimulation of gastric juices, in which chlorogenic acid is absorbed together with the food.

It is known from the publication of J. Ramage entitled "Inhibition of food stimulated acid secretion by misoprostol" that the formation of gastric acid by means of food may be avoided if a synthetic prostaglandin E analog is used (cf. Br. J. Clin. Pharmac. 19, pp. 9-12 (1985).

The object of the invention, therefore, was to find low molecular weight substances, preferably natural substances, which can be used for or in food, which are characterized by better compatibility and higher performance compared to the known active ingredients and where the acid secretion induced by the aforementioned food constituents can be reduced or even completely prevented.

DESCRIPTION OF THE INVENTION

The invention relates to a pharmaceutical preparation comprising bitter-masking acting substances for reducing and/or inhibiting gastric acid secretion induced by food constituents.

It has been found, surprisingly, that substances which are capable of masking the bitterness of many foods, also at the same time reduce or even inhibit the secretion of gastric acid induced by these substances. In particular, it was found that substances of the group (a), such as homoeriodictyol, eriodictyol, matairesinol, lariciresinol or enterolactone, can in combination again reduce or completely block the gastric acid-stimulating effect of the substances of the group (b), such as caffeine or theobromine.

This is all the more astonishing, since up to now it has been assumed that the masking substances only dock onto certain taste receptors and do not even have a pharmacological effect. The use of the masking substances for the stated purpose has the further advantage here that they have already proven to be palatable.

BRIEF DESCRIPTION OF THE DRAWINGS

The present invention will be described in greater detail with reference to the accompanying drawings, in which.

BITTER-MASKING SUBSTANCES (COMPONENT A)

Figure 1:
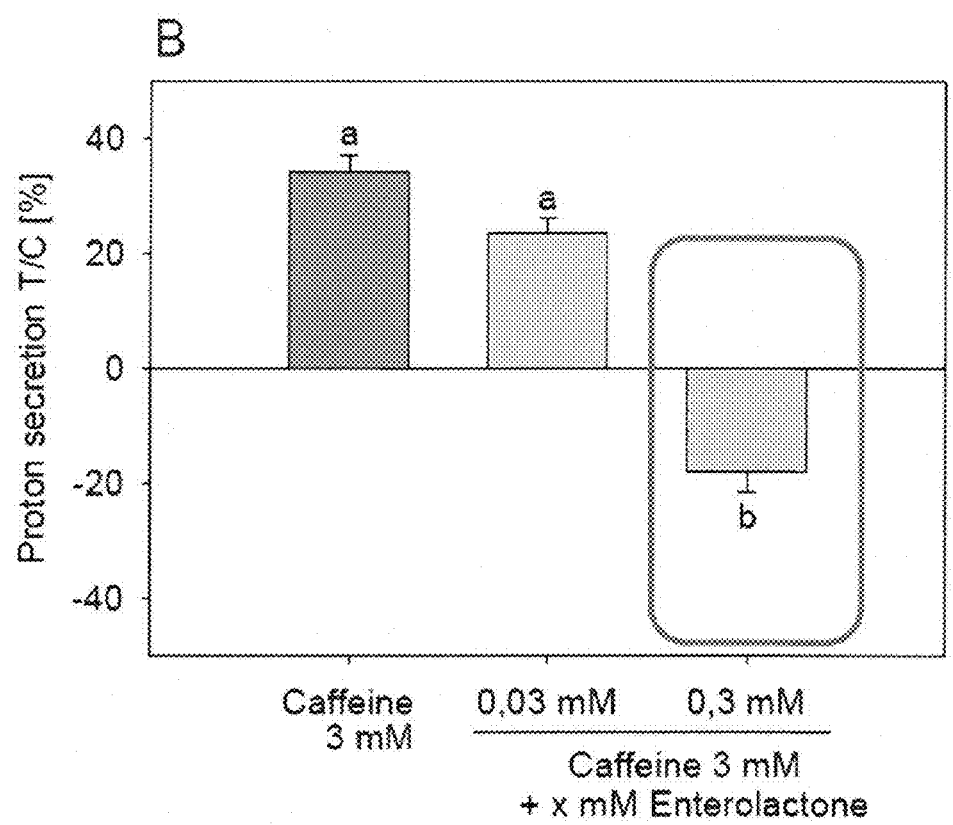
FIG. 1 illustrates a graph of proton secretion on exposure to caffeine or caffeine/enterolactone.

The bitter-masking substances which can form component (a) are selected from the group formed by:
hydroxyflavanones, particularly eriodictyol, eriodictyol-7-methyl ether, homoeriodictyol, and sodium, potassium, calcium, magnesium or zinc salts thereof, especially those which are described in the European patent application EP 1258200 A2;
hydroxybenzamides, particularly those which are described in the international patent application WO 2006 024587 A2;
hydroxyphenylalkanediones, particularly gingerdione-[2] and gingerdione-[3], and especially those which are described in the international patent application WO 2007 003527 A2;
gamma-aminobutyric acid, particularly those which are described in the international patent application WO 2005 096841 A1;
4-hydroxydihydrochalcones, particularly phloretin and those which are disclosed in the international patent application WO 2007 107596 A1;
vanillyl lignans, particularly matairesinol, lariciresinol, hydroxymatairesinol which are disclosed, for example, in the international patent application WO 2012 146, 584, and particularly also
enterolactone.

Bitter-Masking Food Constituents Inducing Secretion of Gastric Acid (Component b)

These substances comprising the component (b) are selected from the group formed by:
xanthines, particularly caffeine, theobromine and theophylline;
fruit acids, particularly tartaric acid, racemic acid, malic acid and succinic acid;
phenolic glycosides, particularly salicin and arbutin;
flavanone glycosides, particularly neohesperedin, eriocitrin, neoeriocitrin, narirutin and naringin;
dihydrochalcone glycosides, particularly phloridzin, trilobatin;
hydrolyzable tannins, particularly gallic or ellagic esters or carbohydrates, e.g. pentagalloyl glucose;
non-hydrolyzable tannins, particularly galloylated catechins or epicatechins and oligomers thereof, e.g. proanthyocyanidins or procyanidins, thearubigins, flavones and glycosides thereof, particularly quercetin, quercitrin, rutin, taxifolin, myricetin, myrictrin;
terpenoid bitter substances, particularly limonin, nomilin, lupolone and humolone;
triterpene glycosides, particualrly steviosides, rubusoside, stevioside, rebaudioside A, rebaudioside C, glycyrrhizin (glycyrrhizic acid) and glycyrrhetic acid; and
iridoid bitter substances such as oleuropein
and mixtures thereof.

Preferred Embodiments

The highest reduction or complete inhibition of the induced gastric acid secretion was observed in preparations which comprised caffeine and/or theobromine as component (b) and to which was added one of the following substances of component (a), namely homoeriodictyol (1), eriodictyol (2), matairesinol (3), lariciresinol (4) and/or enterolactone (5). Corresponding preparations are therefore particularly preferred.

The bitter-masking substances which can form component (a) are selected from the group formed by:
The preferred compounds are shown again in the following Figure:

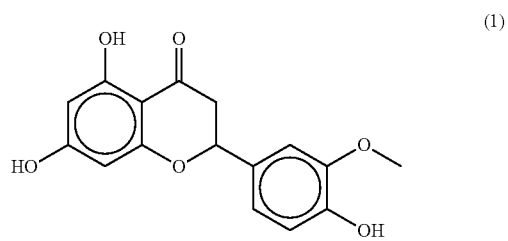

(1)

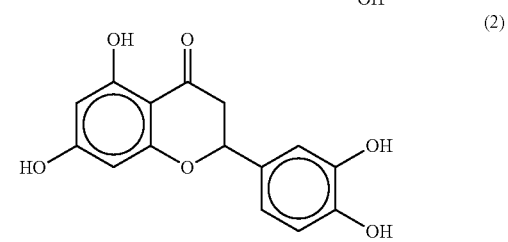

(2)

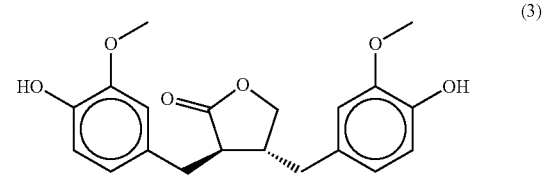

(3)

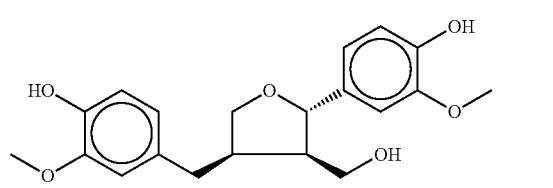

(4)

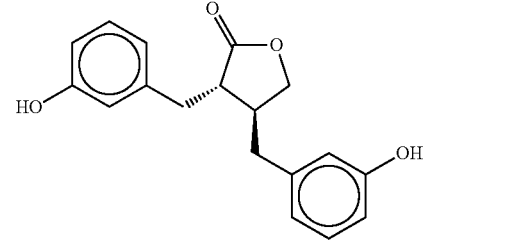

(5)

In principle, the therapeutic preparations may comprise both the substances which form component (a) and (b), in each case in amounts of approximately 0.1 mg/kg (corresponding to 0.1 ppm) to approximately 1% by weight. However, the substances are preferably present in each case in amounts of approximately 0.5 to approximately 1000 mg/kg (corresponding to approximately 0.5 to approximately 1000 ppm), preferably of approximately 1 to approximately 500 mg/kg, more preferably of approximately 3 to approximately 300 mg/kg, particularly preferably of approximately 5 to approximately 200 mg/kg and most preferably of approximately 10 to 100 mg/kg.

The preparations according to the invention may comprise the substances which form components (a) and (b) in the weight ratio of approximately 1:100 to approximately 1:1, preferably 1:90 to approximately 1:2 and particularly of approximately 1:5 to approximately 1:10.

Oral Preparations

The present invention further relates to a preparation for oral administration, specifically providing nutrition or enjoyment, comprising as already elucidated in detail above
(a) bitter-masking acting substances and
(b) substances which induce the secretion of gastric acid.

The preparations providing nutrition or enjoyment (i.e. suitable for consumption) are, in the context of this invention, e.g. bakery products (e.g. bread, dry biscuits, cakes, other baked goods), confectionery (e.g. chocolates, chocolate bar products, other bar products, fruit gums, hard and soft caramels, chewing gum), alcoholic or non-alcoholic drinks (e.g. coffee, tea, wine, wine-based drinks, beer, beverages containing beer, liqueurs, spirits, brandies, fruit-containing carbonated beverages, isotonic drinks, soft drinks, nectars, fruit and vegetable juices, fruit or vegetable juice preparations), instant drinks (e.g. instant cocoa drinks, instant tea drinks, instant coffee drinks), meat products (e.g. ham, fresh or cured sausage, spiced or marinated fresh or cured meat), eggs or egg products (dried egg, egg white, egg yolk), cereal products (e.g. breakfast cereals, muesli bars, precooked instant rice products), dairy products (e.g. milk drinks, ice milk, yogurt, kefir, cream cheese, soft cheese, hard cheese, dried milk powder, whey, butter, buttermilk, partially or fully hydrolyzed milk protein-containing products), products made from soy protein or other soybean fractions (e.g. soy milk and products manufactured therefrom, preparations containing soy lecithin, fermented products such as tofu or tempeh or products manufactured therefrom, soy sauce), fruit preparations (e.g. jams, fruit ice cream, fruit sauces, fruit fillings), vegetable preparations (e.g. ketchup, sauces, dried vegetables, frozen vegetables, precooked vegetables, pickled vegetables, cooked vegetables), snack foods (e.g. baked or fried potato chips or reconstituted potato products, bread dough products, extrudates based on maize or peanut), products based on fat and oil or emulsions of the same (e.g. mayonnaise, remoulade, dressings, seasoning preparations), other ready meals and soups (e.g. dried soups, instant soups, precooked soups), spices, spice mixtures and especially seasonings which are used in the snack food sector.

The oral preparations in the context of the invention may also serve as semi-finished goods for the preparation of further orally consumable preparations. The preparations in the context of the invention may also be in the form of capsules, tablets (oral and/or gastric disintegrating tablets), sugar-coated pills, granules, pellets, mixtures of solids, dispersions in liquid phases, as emulsions, as powders, as solutions, as pastes or as other swallowable or chewable preparations as food supplements.

Preference is given here to incorporating one or more of the substances of group (a) in an orally consumable preparation, particularly in the form of preparations which can be swallowed (e.g. drinks, dispersions, emulsions, pastes, capsules which can dissolve in the mouth or stomach, tablets, compressed products, soft caramels, sugar-coated pills, granules, pellets, fruit gums) or in preparations not intended to be swallowed (e.g. chewing gum, hard caramels) releasing sufficient concentrations of substances of group (a) in an effective concentration.

The substances of group (a) to be used in accordance with the invention in preparations suitable for consumption in accordance with the invention, particularly in the preferred concentrations to be used in accordance with the invention, have no appreciable taste of their own and in particular they have no unpleasant or objectionable flavors at the (preferred or particularly preferred) concentrations employed. The substances of group (a) are each capable alone and/or in mixtures to reduce or to completely block the bitterness of one or more of the substances of group (b).

The substance(s) of group (a) and also preparations according to the invention comprising the substance(s) of group (a), can be fed orally in time sequence before, during or after oral administration of the substance(s) of group (b) or preparations comprising the substance(s) of group (b).

Particularly advantageous here is the known fact that the substances of group (a) are regularly capable of partially or completely reducing the bitter (unpleasant) taste of the substances of group (b) and therefore can significantly increase the acceptability of the preparations. This is particularly the case if the substances of group (b) are applied at the same time as the substances of group (a).

In the case of subsequent oral administration of the substance(s) of group (a), preparation forms are preferred which comprise the substance(s) of group (a) in a form which causes delayed release.

In an alternative to the simultaneous oral administration, preparations may also be suitable which have one or more of the unpleasant tasting and gastric acid-stimulating substances of group (b) in an effective amount with respect to gastric acid stimulation and simultaneously comprise one or more of the substances of group (a) in an effective amount with respective to gastric acid stimulation.

In principle, the oral preparations may comprise—be they finished or semi-finished products—both the substances which form component (a) and (b), in each case in amounts of approximately 0.1 mg/kg (corresponding to 0.1 ppm) to approximately 1% by weight. However, the substances are preferably present in each case in amounts of approximately 0.5 to approximately 1000 mg/kg (corresponding to approximately 0.5 to approximately 1000 ppm), preferably of approximately 1 to approximately 500 mg/kg, more preferably of approximately 3 to approximately 300 mg/kg, particularly preferably of approximately 5 to approximately 200 mg/kg and most preferably of approximately 10 to 100 mg/kg.

The preparations according to the invention may comprise the substances which form components (a) and (b) in the weight ratio of approximately 1:100 to approximately 1:1, preferably 1:90 to approximately 1:2 and particularly of approximately 1:5 to approximately 1:10.

INDUSTRIAL APPLICABILITY

A preferred method for determining the desired effect of substances of group (a) on decreasing the effect of substances of group (b) consists of measuring the intracellular pH of HGT-1 cell cultures (human gastric tumor cell line) after treatment with the test substances as described in Liszt, K. I.; Walker, J.; Somoza, V. *J. Agric Food Chem.* 2012, 60, (28), 7022-7030. To date, only the somatostatin receptor (SSTR2) on the cell surface of gastric acid-secreting cells has been described as a target for reducing the secretion; this receptor has also been described in HGT-1 To date, these cells have only ever been brought into contact with potential SSTR2 regulators; the co-administration of bitter agonists and potential antagonists has not been described to date.

Two further aspects of the present invention relate firstly to a non-therapeutic method for reducing and/or inhibiting secretion of gastric acid induced by food constituents, in which an effective amount of a bitter-masking acting substance is orally administered to a human or animal, and secondly the use of bitter-masking acting substances for reducing and/or inhibiting the secretion of gastric acid induced by food constituents. With regard to the nature of the substances and the amounts used thereof, reference is made to the embodiments above which are fully incorporated here.

EXAMPLES

Cell Model

Human parietal cells, also known as human gastric tumor cell line (HGT-1), are used as cell model. These were provided by Dr. C. Laboisse (Laboratory of Pathological Anatomy, Nantes, France). The cells were cultured under standard conditions at 37° C., 5% $CO_2$ in DMEM (Dulbecco's Modified Eagle's Medium) with 4 g/l glucose, 10% FBS, 2% L-glutamine and 1% penicillin/streptomycin. For the measurement of the intracellular proton concentration, the cells are treated with trypsin/EDTA, the viability determined by means of trypan blue staining and 100 000 cells/well seeded in black 96-well plates.

Example 1

Determination of the Intracellular pH of HGT-1 Cell Cultures in the Presence of the Substances of Group (a) and Substances of Group (b)

To measure the intracellular pH, the dye 1,5-carboxyseminaphthorhodafluoro acetoxymethyl ester (SNARF-1-AM) is used. The cells in the 96-well plates are washed once with Krebs-Hepes buffer (KRHP) and incubated at 37° C. and 5% $CO_2$ for 30 min with the dye dissolved in KRHP at a concentration of 3 µM. The cells are then washed twice with KRHP and substances of group (b), for example 3 mM caffeine or 0.3 mM theobromine, alone or in combination with substances of group (a), for example, homoeriodictyol (HED) or eriodictyol or matairesinol, lariciresinol or enterolactone, are applied in volumes of 100 µl at various concentrations in phenol red-free DMEM; as additional control experiments, the abovementioned substances of group (a) are tested alone. Homoeriodictyol is dissolved in double-distilled water while eriodictyol, matairesinol, lariciresinol or enterolactone are dissolved in ethanol (EtOH). The final concentration of solvent which is added to the cells is at most 1%. The fluorescent dye is excited at a wavelength of 488 nm and the emission measured at 580 nm and 640 nm. The ratio of the fluorescence values at 580 nm to 640 nm is compared to a calibration curve from which the pH can be determined. For the calibration curve, the cells are treated with a potassium phosphate buffer of different pH values from pH 7.2-8.2 and 2 µM nigericin. Nigericin equilibrates the intracellular and extracellular pH such that the intracellular pH may be defined. The intracellular $H^+$ concentration is determined from the intracellular pH. The intracellular proton index (IPX) is calculated by log 2 transformation of the ratio of treated cells and untreated cells (control). The results given here are stated as percentage changes compared to untreated control cells (cf. Malte Rubach, R. L., Elisabeth Seebach, Mark M. Somoza, Thomas Hofmann; Somoza, a. V., Mol Nutr Food Res. in press, 2011; Rubach, M.; Lang, R.; Hofmann, T.; Somoza, V., *Ann N Y Acad Sci* 2008, 1126, 310-4; Rubach, M.; Lang, R.; Skupin, C.; Hofmann, T.; Somoza, V., *J Agric Food Chem* 2010, 58, 4153-61; Weiss, C.; Rubach, M.; Lang, R.; Seebach, E.; Blumberg, S.; Frank, O.; Hofmann, T.; Somoza, V., *J Agric Food Chem* 2010, 58, 1976-85; Liszt, K. I.; Walker, J.; Somoza, V., *J Agric Food Chem* 2012; Walker, J.; Hell, J.; Liszt, K. I.; Dresel, M.; Pignitter, M.; Hofmann, T.; Somoza, V., *J Agric Food Chem* 2012, 60, 1405-12). The number of replicates specified refers to the technical replicates (tr) or the number or total replicates (n), which results from the number of technical replicates multiplied by the number of biological replicates.

Given in Table 1A below is the percentage increase of the proton secretion in HGT-1 cells compared to untreated controls after 10 minutes stimulation by DMEM or DMEM with 1% ETOH or 1 mM histamine or 3 mM caffeine with and without 1% EtOH. The data are presented as mean values and mean standard deviations, n=21-37, tr=6. Statisitics: one-way Anova with post-hoc test according to Dunn. Significant differences (p<0.05) are indicated by letters.

TABLE 1A

| Comparative Example, increase in secretion due to substances of group (b). | | |
|---|---|---|
| Test substance | T/C [%] | SEM |
| Control (DMEM) | 0.150 | 1.00 a |
| EtOH 1% | 14.44 | 2.61 b |
| 1 mM Histamine | 27.42 | 3.17 b |
| 3 mM Caffeine | 48.87 | 3.64 d |
| 3 mM Caffeine + 1% EtOH | 44.92 | 3.51 d |

Given in Table 1B below is the percentage increase of the proton secretion in HGT-1 cells compared to untreated controls after 10 minutes stimulation by DMEM or DMEM with 1% ETOH or 1 mM histamine or 0.3 mM theobromine with and without 1% EtOH. The data are presented as mean values and mean standard deviations, n=21-37, tr=6. Statisitics: one-way Anova with post-hoc test according to Dunn. Significant differences (p<0.05) are indicated by letters.

TABLE 1B

| Comparative Example, increase in secretion due to substances of group (b). | | |
|---|---|---|
| Test substance | T/C [%] | SEM |
| DMEM (control) | 0.15 | 1.00 a |
| 1% EtOH | 14.44 | 2.61 b |
| 1 mM Histamine | 27.42 | 3.17 b, c |
| 0.3 mM Theobromine | 17.51 | 2.65 b |
| 0.3 mM Theobromine + 1% EtOH | 32.11 | 2.49 c, d |

Given in Table 2A below is the percentage increase of the proton secretion in HGT-1 cells compared to untreated controls after 10 minutes stimulation by DMEM (control) or homoeriodictyol (HED) at various concentrations. The data are presented as mean values and mean standard deviations, n=4, tr=6. Statisitics: one-way Anova with post-hoc test according to Dunn. Significant differences (p<0.05) are indicated by letters.

TABLE 2A

| Influence on the secretion by substances of group (a). | | |
|---|---|---|
| Test substance | T/C [%] | SEM |
| DMEM (control) | −1.43 | 2.01 a |
| 0.003 mM HED | −8.04 | 3.88 a |
| 0.03 mM HED | 12.70 | 4.02 a |
| 0.3 mM HED | −3.66 | 5.24 a |

Given in Table 2B below is the percentage increase of the proton secretion in HGT-1 cells compared to untreated controls after 10 minutes stimulation by DMEM (control) or eriodictyol at various concentrations. The data are presented as mean values and mean standard deviations, n=3-7, tr=6.

Statisitics: one-way Anova with post-hoc test according to Dunn. Significant differences (p<0.05) are indicated by letters.

TABLE 2B

Influence on the secretion by substances of group (a).

| Test substance | T/C [%] | SEM |
|---|---|---|
| Control (DMEM) | 0.98 | 2.30 a |
| 0.03 mM Eriodictyol | −10.77 | 11.16 a |
| 0.3 mM Eriodictyol | −11.67 | 7.25 a |

Given in Table 2C below is the percentage increase of the proton secretion in HGT-1 cells compared to untreated controls after 10 minutes stimulation by 3 mM caffeine or 3 mM caffeine in combination with matairesinol at various concentrations. The data are presented as mean values and mean standard deviations, n=8, tr=6. Statisitics: one-way Anova with post-hoc test according to Dunn. Significant differences (p<0.05) are indicated by letters.

TABLE 2C

Influence on the secretion by substances of group (a).

| Test substance | T/C [%] | SEM |
|---|---|---|
| DMEM (control) | −0.63 | 1.70 a |
| 0.03 mM Matairesinol | −9.40 | 3.73 a |
| 0.3 mM Matairesinol | −31.69 | 2.95 b |

Given in Table 2D below is the percentage increase of the proton secretion in HGT-1 cells compared to untreated controls after 10 minutes stimulation by DMEM (control) or lariciresinol at various concentrations. The data are presented as mean values and mean standard deviations, n=8, tr=6. Statisitics: one-way Anova with post-hoc test according to Dunn. Significant differences (p<0.05) are indicated by letters.

TABLE 2D

Influence on the secretion by substances of group (a).

| Test substance | T/C [%] | SEM |
|---|---|---|
| Control (DMEM) | 0.15 | 1.93 a |
| 0.03 mM Lariciresinol | 6.40 | 4.46 a |
| 0.3 mM Lariciresinol | −2.04 | 2.78 a |

Given in Table 2E below and also FIG. 1 is the percentage increase of the proton secretion in HGT-1 cells compared to untreated controls after 10 minutes stimulation by DMEM (control) or enterolactone at various concentrations. The data are presented as mean values and mean standard deviations, n=8, tr=6. Statisitics: one-way Anova with post-hoc test according to Dunn. Significant differences (p<0.05) are indicated by letters.

TABLE 2E

Influence on the secretion by substances of group (a).

| Test substance | T/C [%] | SEM |
|---|---|---|
| Control (DMEM) | −2.28 | 1.80 a |
| 0.03 mM Enterolactone | −2.76 | 3.75 a |
| 0.3 mM Enterolactone | −27.31 | 4.43 a |

Given in Table 3A below is the percentage increase of the proton secretion in HGT-1 cells compared to untreated controls after 10 minutes stimulation by 3 mM caffeine or 3 mM caffeine in combination with homoeriodictyol (HED) at various concentrations. The data are presented as mean values and mean standard deviations, n=4, tr=6. Statisitics: one-way Anova with post-hoc test according to Dunn. Significant differences (p<0.05) are indicated by letters.

TABLE 3A

Decrease in the secretion, triggered by substances of group (b), by substances of group (a)

| Test substance | T/C [%] | SEM |
|---|---|---|
| 3 mM Caffeine | 54.79 | 5.61 a |
| 3 mM Caffeine + 0.03 mM HED | 37.99 | 6.70 a |
| 3 mM Caffeine + 0.3 mM HED | 20.18 | 5.99 b |

Given in Table 3B below is the percentage increase of the proton secretion in HGT-1 cells compared to untreated controls after 10 minutes stimulation by 3 mM caffeine or 3 mM caffeine in combination with eriodictyol at various concentrations. The data are presented as mean values and mean standard deviations, n=4, tr=6. Statisitics: one-way Anova with post-hoc test according to Dunn. Significant differences (p<0.05) are indicated by letters.

TABLE 3B

Decrease in the secretion, triggered by substances of group (b), by substances of group (a)

| Test substance | T/C [%] | SEM |
|---|---|---|
| 3 mM Caffeine | 54.05 | 4.37 a |
| 3 mM Caffeine + 0.03 mM Eriodictyol | 29.69 | 8.82 a |
| 3 mM Caffeine + 0.3 mM Eriodictyol | −33.96 | 7.55 b |

Given in Table 3C below is the percentage increase of the proton secretion in HGT-1 cells compared to untreated controls after 10 minutes stimulation by 3 mM caffeine or 3 mM caffeine in combination with matairesinol at various concentrations. The data are presented as mean values and mean standard deviations, n=4, tr=6. Statisitics: one-way Anova with post-hoc test according to Dunn. Significant differences (p<0.05) are indicated by letters.

TABLE 3C

Decrease in the secretion, triggered by substances of group (b), by substances of group (a)

| Test substance | T/C [%] | SEM |
|---|---|---|
| 3 mM Caffeine | 38.75 | 2.63 a |
| 3 mM Caffeine + 0.03 mM Matairesinol | 14.39 | 3.55 b |
| 3 mM Caffeine + 0.3 mM Matairesinol | −20.43 | 4.82 c |

Reproduced in Table 3D below is the percentage increase of the proton secretion in HGT-1 cells compared to untreated controls after 10 minutes stimulation by 3 mM caffeine or 3 mM caffeine in combination with lariciresinol at various concentrations. The data are presented as mean values and mean standard deviations, n=5, tr=6. Statisitics: one-way Anova with post-hoc test according to Dunn. Significant differences (p<0.05) are indicated by letters.

TABLE 3D

Decrease in the secretion, triggered by substances of group (b), by substances of group (a)

| Test substance | T/C [%] | SEM |
| --- | --- | --- |
| 3 mM Caffeine | 52.41 | 4.16 a |
| 3 mM Caffeine + 0.03 mM Lariciresinol | 46.40 | 3.98 a |
| 3 mM Caffeine + 0.3 mM Lariciresinol | 21.57 | 3.78 b |

Figure 2:
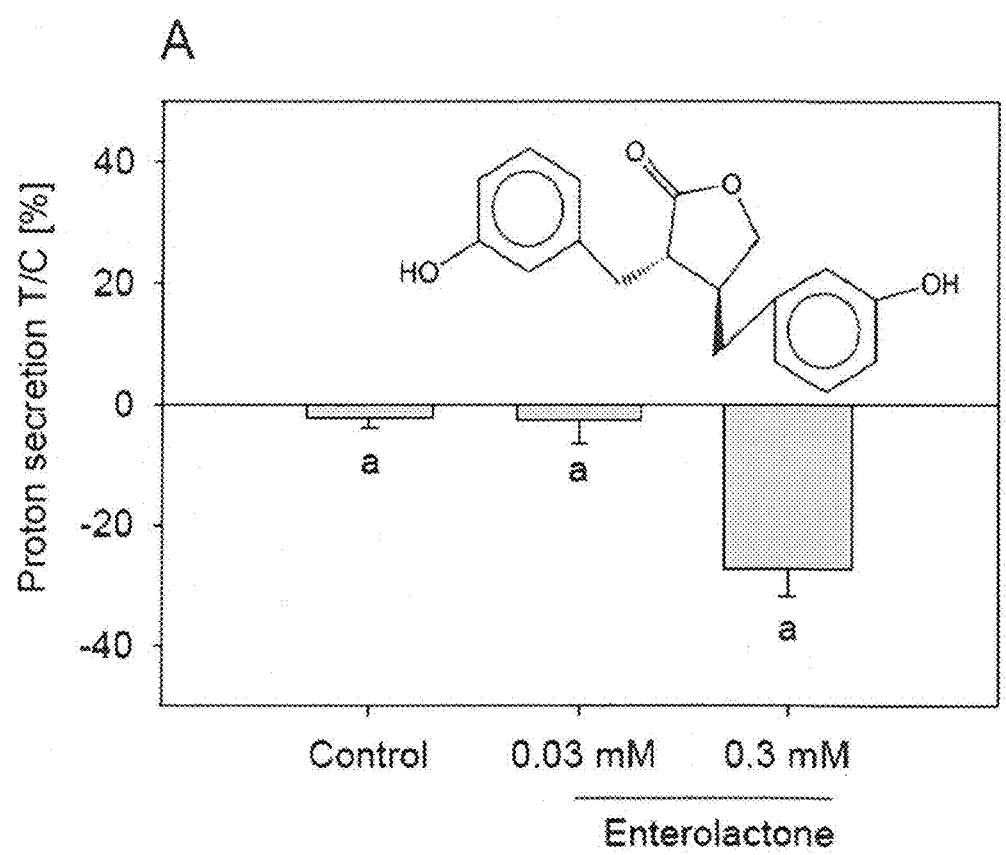
FIG. 2 illustrates a graph of proton secretion on exposure to enterolactone

Reproduced in Table 3E below and also FIG. 2 is the percentage increase of the proton secretion in HGT-1 cells compared to untreated controls after 10 minutes stimulation by 3 mM caffeine or 3 mM caffeine in combination with enterolactone at various concentrations. The data are presented as mean values and mean standard deviations, n=5, tr=6. Statisitics: one-way Anova with post-hoc test according to Dunn. Significant differences (p<0.05) are indicated by letters.

TABLE 3E

Decrease in the secretion, triggered by substances of group (b), by substances of group (a)

| Test substance | T/C [%] | SEM |
| --- | --- | --- |
| 3 mM Caffeine | 34.12 | 2.86 a |
| 3 mM Caffeine + 0.03 mM Enterolactone | 23.41 | 2.56 a |
| 3 mM Caffeine + 0.3 mM Enterolactone | −18.25 | 3.39 b |

Reproduced in Table 3F below is the percentage increase of the proton secretion in HGT-1 cells compared to untreated controls after 10 minutes stimulation by 0.3 mM theobromine or 0.3 mM theobromine in combination with homoeriodictyol (HED) at various concentrations. The data are presented as mean values and mean standard deviations, n=3, tr=6. Statisitics: one-way Anova with post-hoc test according to Dunn. Significant differences (p<0.05) are indicated by letters.

TABLE 3F

Decrease in the secretion, triggered by substances of group (b), by substances of group (a)

| Test substance | T/C [%] | SEM |
| --- | --- | --- |
| 0.3 mM Theobromine | 20.92 | 3.37 a |
| 0.3 mM Theobromine + 0.003 mM HED | 21.56 | 2.33 a |
| 0.3 mM Theobromine + 0.03 mM HED | 13.79 | 3.50 a |
| 0.3 mM Theobromine + 0.3 mM HED | −16.92 | 3.27 b |

Reproduced in Table 3G below is the proton secretion in HGT-1 cells after 10 minutes stimulation by 0.3 mM theobromine or 0.3 mM theobromine in combination with eriodictyol at various concentrations. The data are presented as mean values and mean standard deviations, n=3, tr=6. Statisitics: one-way Anova with post-hoc test according to Dunn. Significant differences (p<0.05) are indicated by letters.

TABLE 3G

Decrease in the secretion, triggered by substances of group (b), by substances of group (a)

| Test substance | T/C [%] | SEM |
| --- | --- | --- |
| 0.3 mM Theobromine | 47.64 | 5.28 a |
| 0.3 mM Theobromine + 0.03 mM Eriodictyol | 23.95 | 4.17 b |
| 0.3 mM Theobromine + 0.3 mM Eriodictyol | −42.86 | 9.73 c |

Reproduced in Table 3H below is the proton secretion in HGT-1 cells after 10 minutes stimulation by 0.3 mM theobromine or 0.3 mM theobromine in combination with matairesinol at various concentrations. The data are presented as mean values and mean standard deviations, n=3, tr=6. Statisitics: one-way Anova with post-hoc test according to Dunn. Significant differences (p<0.05) are indicated by letters.

TABLE 3H

Decrease in the secretion, triggered by substances of group (b), by substances of group (a)

| Test substance | T/C [%] | SEM |
| --- | --- | --- |
| 0.3 mM Theobromine | 34.12 | 2.86 a |
| 0.3 mM Theobromine + 0.03 mM Matairesinol | 23.41 | 2.56 b |
| 0.3 mM Theobromine + 0.3 mM Matairesinol | −18.25 | 3.39 c |

Reproduced in Table 3I below is the percentage increase of the proton secretion in HGT-1 cells compared to untreated controls after 10 minutes stimulation by 0.3 mM theobromine or 0.3 mM theobromine in combination with lariciresinol at various concentrations. The data are presented as mean values and mean standard deviations, n=3, tr=6. Statisitics: one-way Anova with post-hoc test according to Dunn. Significant differences (p<0.05) are indicated by letters.

TABLE 3I

Decrease in the secretion, triggered by substances of group (b), by substances of group (a)

| Test substance | T/C [%] | SEM |
| --- | --- | --- |
| 0.3 mM Theobromine | 30.81 | 3.44 a |
| 0.3 mM Theobromine + 0.03 mM Lariciresinol | 31.73 | 5.80 a |
| 0.3 mM Theobromine + 0.3 mM Lariciresinol | 17.55 | 3.67 a |
| | | (t-test p < 0.05) |

As follows from Tables 1A and 1B, the proton secretion in the HGT-1 cells is stimulated by substances of group (b), in this case caffeine or theobromine, which effectively triggers acid secretion into the extracellular space. The substances of group (a) alone lead either to no significant effect (Tables 2A, 2B and 2D) or even to a significant decrease of the constitutive acid secretion (Table 2C). The stimulation of proton secretion by 3 mM caffeine (Tables 3A-3E) or 0.3 mM theobromine (Tables 3F-3I) could be reduced or completely inhibited by additional administration of the substances of group (a), particularly homoeriodictyol, eriodictyol, matairesinol, lariciresinol or enterolactone at a concentration of 0.3 mM.

Application Example 1

Spray-Dried Preparation as Semi-Finished Goods for Preparing Finished Goods

Drinking water is placed in a container and maltodextrin and gum arabic dissolved therein. The substances of group (a) are then emulsified in the carrier solution using a Turrax. The temperature of the spray solution should not exceed 30° C. The mixture is then spray-dried (nominal temperature at the start: 185-195° C., nominal temperature at the end: 70-75° C.). The spray-dried semi-finished goods comprise ca. 18-22% of the compounds of group (a).

TABLE 4

Semi-finished goods composition - amounts in % by weight.

| Preparation | A | B | C | D | E |
|---|---|---|---|---|---|
| Drinking water | 60.8 | 60.8 | 60.8 | 60.8 | 60.8 |
| Maltodextrin from wheat | 24.3 | 24.3 | 24.3 | 24.3 | 24.3 |
| Gum arabic | 6.1 | 6.1 | 6.1 | 6.1 | 6.1 |
| Matairesinol | 8.8 | — | 4.4 | — | — |
| Homoeriodictyol | — | 8.8 | 4.4 | — | — |
| Eriodictyol | — | — | — | 8.8 | — |
| Enterolactone | — | — | — | — | 8.8 |

Application Example 2

Drinkable Iced Tea Preparation

The compounds of group (a) were each pre-dissolved at 10% in ethanol. Black tea extract was dissolved in water and stirred in a glass beaker together with sugar, a flavoring preparation (peach flavor) and the ethanolic solutions of the compounds of group (a).

TABLE 5

Iced tea composition - amounts in % by weight.

| Preparation | A | B |
|---|---|---|
| Black tea extract | 1.4 | 1.4 |
| Water | 89.5 | 89.5 |
| Flavoring preparation (peach type) | 0.65 | 0.65 |
| Sugar | 7.0 | 7.0 |
| Citric acid (crystalline) | 1.2 | 1.2 |
| Ascorbic acid | 0.2 | 0.2 |
| Matairesinol in ethanol (10%) | 0.05 | — |
| Homoeriodictyol in ethanol (10%) | — | 0.05 |

Application Example 3

Gelatine Capsules without Substances of Group (b) for Direct Consumption after Application of Substances of Group (b)

The gelatine capsules suitable for direct consumption were prepared according to WO 2004/050069 and had a diameter of 5 mm and the ratio by weight of core material to shell material was 90:10. The capsules opened in the mouth within less than 10 seconds and dissolved completely in less than 50 seconds.

TABLE 6

Gelatine capsule composition - amounts in % by weight.

| Ingredients | A | B | C |
|---|---|---|---|
| Gelatine shell: | | | |
| Glycerol | 2.014 | 2.014 | 2.014 |
| Gelatine 240 Bloom | 7.91 | 7.91 | 7.91 |
| Sucralose | 0.065 | 0.065 | 0.065 |
| Allura red | 0.006 | — | 0.011 |
| Brilliant blue | 0.005 | 0.011 | — |
| Core composition | | | |
| Vegetable oil triglyceride (coconut oil fraction) | 79.49 | 68.55 | 58.55 |
| Orange flavoring comprising 1% by weight homoeriodictyol based on the total weight of the flavoring. | 10.0 | — | — |
| Peppermint flavoring comprising 1% by weight matairesinol based on the total weight of the flavoring | — | 20.0 | — |
| Cherry flavoring comprising 1% by weight enterolactone based on the total weight of the flavoring. | — | — | 28.65 |
| Rebaudioside A 98% | 0.05 | 0.05 | — |
| 2-Hydroxypropylmenthylcarbonate | 0.33 | 0.20 | — |
| 2-Hydroxyethylmenthylcarbonate | — | 0.20 | 1.00 |
| (1R,3R,4S) Menthyl-3-carboxylic acid N-ethylamide (WS-3) | — | 0.55 | — |
| (−)-Menthyl lactate (Frescolat ML) | — | 0.30 | — |
| Vanillin | 0.07 | — | 0.10 |

Application Example 4

Chewing Gum without Substances of Group (b)

Parts A to D are mixed and kneaded intensively. The crude mass may be processed, for example in the form of thin strips, to form ready-to-consume chewing gum.

TABLE 7

Chewing gum composition - amounts in % by weight.

| Part | Preparation | A | B |
|---|---|---|---|
| A | Chewing gum base, "Jagum T" company | 30.00 | 30.00 |
| B | Sorbitol, powdered | 39.00 | 39.00 |
| | Isomalt ® (Palatinit GmbH) | 9.50 | 9.50 |
| | Xylitol | 2.00 | 2.00 |
| | Mannitol | 3.00 | 3.00 |
| | Aspartame ® | 0.10 | 0.10 |
| | Acesulfame ® K | 0.10 | 0.10 |
| | Emulgum ® (Colloides Naturels, Inc.) | 0.30 | 0.30 |
| C | Sorbitol, 70% | 14.00 | 14.00 |
| | Glycerol | 1.00 | 1.00 |
| D | Mint flavoring comprising 1% matairesinol based on the total weight of the flavoring. | 1.00 | — |
| | Tutti frutti flavoring comprising 1% homoeriodictyol based on the total weight of the flavoring. | — | 2.00 |

Application Example 5

Use in a Soluble Cappuccino Drink

The specified raw materials are mixed. In each case 12.5 g of the prepared instant cappuccino powder are dissolved in 150 ml of hot water.

TABLE 8

Cappuccino drink composition - amounts in % by weight.

| Preparation | A | B |
|---|---|---|
| Coffee extract, spray-dried | 14.0 | 16.0 |
| Sugar | 28.3 | 25.3 |

TABLE 8-continued

Cappuccino drink composition - amounts in % by weight.

| Preparation | A | B |
|---|---|---|
| Fat powder | 18.2 | 18.2 |
| Coffee whitener, foaming | 30.0 | 28.0 |
| Hydrocolloids/emulsifiers | 1.8 | 1.8 |
| Lactose | 4.7 | 4.7 |
| Semi-finished product A from application example 1 | 3.0 | — |
| Semi-finished product B from application example 1 | — | 6.0 |

Application Example 6

Tea Drink

The tea and the semi-finished goods are mixed and packed in tea bags made of filter paper. To use, one tea bag is infused in 100-250 ml of boiling water and left to draw for 2-5 min.

TABLE 9

Tea drink composition - amounts in % by weight.

| Preparation | A | B | C |
|---|---|---|---|
| Black tea, Ceylon, leaf product | 94.00 | — | — |
| Green tea, China, leaf product | — | 91.90 | — |
| Mate tea, Peru, leaf product | — | — | 95.00 |
| Semi-finished product A from application example 2 | 6.0 | — | — |
| Semi-finished product B from application example 2 | — | 8.0 | — |
| Semi-finished product C from application example 2 | — | — | 5.0 |
| Flavor (lemon type) | — | 0.1 | — |

Application Example 7

Use in a Bitter Chocolate

A bitter chocolate was prepared from the following raw materials and subsequently poured into rectangular forms.

TABLE 10

Chocolate composition - amounts in % by weight.

| Preparation | A | B |
|---|---|---|
| Cocoa mass | 55.55 | 55.55 |
| Cocoa butter | 11.70 | 11.70 |
| Sugar | 29.50 | 29.50 |
| Skimmed milk | 3.00 | 3.00 |
| Lecithin | 0.2 | 0.2 |
| Vanillin | 0.035 | 0.035 |
| 10% Matairesinol in ethanol | — | 0.05 |
| 10% Homoeriodictyol in ethanol | 0.05 | — |

Application Example 8

Sugar-Free Hard Caramel

Palatinit was mixed with water and the mixture melted at 165° C. and subsequently cooled to 115° C. The remaining constituents were added and, after mixing, poured into molds, removed from the molds after solidification and then individually packaged.

TABLE 11

Caramel composition - amounts in % by weight.

| Preparation | A | B | C | D |
|---|---|---|---|---|
| Palatinat, type M | 75.00 | 74.00 | 75.50 | 75.00 |
| Citric acid | — | 1.0 | 0.5 | — |
| Water | 24.88 | 24.842 | 23.88 | 24.844 |
| Yellow coloring | — | 0.01 | — | — |
| Red coloring | — | — | 0.01 | — |
| Blue coloring | 0.01 | — | — | 0.01 |
| Peppermint flavoring | 0.1 | — | — | 0.1 |
| Lemon flavoring | — | 0.1 | — | — |
| Red fruit flavoring | — | — | 0.1 | — |
| Rebaudioside A 98% | — | 0.040 | — | 0.040 |
| Hesperetin | — | 0.001 | — | 0.001 |
| Phloretin | — | 0.002 | — | — |
| Homoeriodictyol | 0.010 | 0.005 | — | 0.005 |
| Matairesinol | — | 0.005 | — | — |
| Eriodictyol | — | — | 0.010 | — |
| Enterolactone | — | — | — | 0.005 |

The invention claimed is:

1. A pharmaceutical preparation, comprising
   (a) a food constituent inducing gastric acid secretion and which is caffeine, and
   (b) a bitter-masking acting substance for reducing and/or inhibiting gastric acid secretion induced by said food constituent and which is enterolactone, wherein
   the food constituent is present in an amount of from about 3 to about 300 ppm, calculated on the preparation, and
   said bitter-masking acting substance is present in an amount effective to reduce or inhibit proton secretion in HGT-1 cells upon ingestion.

2. The preparation as claimed in claim 1, wherein said preparation comprises the bitter-masking acting substance and the food constituent which form components (a) and (b) in the weight ratio of 1:100 to 1:1.

3. A composition for oral administration comprising the preparation of claim 1.

4. The composition as claimed in claim 3, wherein said composition is in the form of bakery products, confectionery, alcoholic or non-alcoholic drinks, meat products, eggs or egg products, cereal products, milk products, products made from soy protein or other soybean fractions, fruit preparations, vegetable preparations, snack foods, products based on fat and oil or emulsions of the same, other ready meals and soups, spices, spice mixtures and seasonings.

5. The composition as claimed in claim 3, wherein said composition is in the form of a capsule.

6. The preparation as claimed in claim 1, wherein (b) the bitter-masking acting substance is present in an amount of from about 3 to about 300 ppm.

7. The preparation as claimed in claim 6, wherein (b) the bitter-masking acting substance is present in an amount of from about 10 to about 100 ppm.

8. A composition for oral administration comprising a pharmaceutical preparation, comprising
   (a) a food constituent inducing gastric acid secretion, and
   (b) a bitter-masking acting substance for reducing and/or inhibiting gastric acid secretion induced by said food constituent, wherein
   the bitter-masking acting substance (component b) is matairesinol,
   the food constituent inducing gastric acid secretion (component a) is selected from the group consisting of caffeine, theobromine, theophylline, tartaric acid, racemic acid, malic acid, succinic acid, salicin, arbutin, neohesperidin, eriocitrin, neoeriocitrin, narirutin, naringin, phloridzin, trilobatin, gallic and ellagic esters of carbohydrates, galloylated catechins and epicatechins and oligomers thereof, proanthocyanidins, procyanidins, thearubigin, quercetin, quercitrin, rutin, taxifolin, myricetin, myricitrin, limonin, nomilin, lupolone, humolone, stevioside, rubodid, rebaudioside A rebaudioside C, glycyrrhizin, glycyrrhetic acid and oleuropein and mixtures thereof, the food constituent is present in an amount of from about 3 to about 300 ppm, calculated on the preparation, said bitter-masking acting substance is present in an amount effective to reduce or inhibit proton secretion in HGT-1 cells upon ingestion, and said composition is in the form of a capsule.

9. A composition for oral administration comprising a pharmaceutical preparation, comprising (a) a food constituent inducing gastric acid secretion and selected from the group consisting of caffeine, theobromine, theophylline, tartaric acid, racemic acid, malic acid, succinic acid, salicin, arbutin, neohesperidin, eriocitrin, neoeriocitrin, narirutin, naringin, phloridzin, trilobatin, gallic and ellagic esters of carbohydrates, galloylated catechins and epicatechins and oligomers thereof, proanthocyanidins, procyanidins, thearubigin, quercetin, quercitrin, rutin, taxifolin, myricetin, myricitrin, limonin, nomilin, lupolone, humolone, stevioside, rubodid, rebaudioside A, rebaudioside C, glycyrrhizin, glycyrrhetic acid and oleuropein and mixtures thereof, (b) a bitter-masking acting substance for reducing and/or inhibiting gastric acid secretion induced by said food constituent and which is matairesinol, and (c) one of bakery products, confectionery, alcoholic drinks, meat products, eggs or egg products, cereal products, milk products, products made from soy protein or other soybean fractions, fruit preparations, vegetable preparations, snack foods, products based on fat and oil or emulsions of the same, other ready meals and soups, spices, spice mixtures and seasonings, wherein the food constituent is present in an amount of from about 3 to about 300 ppm, calculated on the preparation, and said bitter-masking acting substance is present in an amount effective to reduce or inhibit proton secretion in HGT-1 cells upon ingestion.

10. The preparation as claimed in claim 9, wherein the food constituent is caffeine.

11. The preparation as claimed in claim 9, wherein (b) the bitter-masking acting substance is present in an amount of from about 10 to about 100 ppm.

12. The preparation as claimed in claim 9, wherein said preparation comprises the bitter-masking acting substance and the food constituent which form components (a) and (b) in the weight ratio of 1:100 to 1:1.

* * * * *